United States Patent [19]

Thiele et al.

[11] Patent Number: 4,483,999

[45] Date of Patent: Nov. 20, 1984

[54] PHENOXY ALKANOIC ACID DERIVATIVES HAVING THE ABILITY TO LOWER THE LEVEL OF FATTY SUBSTANCES IN THE BLOOD

[75] Inventors: Kurt Thiele, Zofingen; Quazi Ahmed, Strengelbach; Rudolf Adrian, Vordemwald; Ulrich Jahn, Zofingen, all of Switzerland

[73] Assignee: Siegfried Aktiengesellschaft, Zofingen, Switzerland

[21] Appl. No.: 773,148

[22] Filed: Mar. 1, 1977

Related U.S. Application Data

[63] Continuation-in-part of Ser. No. 536,120, Dec. 24, 1979, abandoned.

[30] Foreign Application Priority Data

Dec. 27, 1973 [CH] Switzerland .................. 18144/73
Nov. 18, 1974 [CH] Switzerland .................. 15329/74

[51] Int. Cl.³ .................................... C07C 69/76
[52] U.S. Cl. ............................ 560/57; 562/468; 424/308
[58] Field of Search ............... 260/520 C; 560/57; 562/468

[56] References Cited

U.S. PATENT DOCUMENTS 3,262,850  7/1966  Jones et al. ................... 560/62
3,362,997  1/1968  Bolhofer et al. ............... 560/62
3,716,583  2/1973  Nakanura et al. ............ 260/520 C
4,088,474  5/1978  Matterstock et al. ............ 71/108

FOREIGN PATENT DOCUMENTS 2356655  5/1974  Fed. Rep. of Germany ... 260/520 C

OTHER PUBLICATIONS

Miyoshi et al., J. Pharm. Soc. Japan, 94(9), pp. 1061-1069 (1974).

Primary Examiner—Paul J. Killos
Attorney, Agent, or Firm—Finnegan, Henderson, Farabow, Garrett & Dunner

[57] ABSTRACT

Novel compounds of the formula

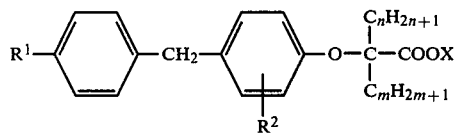

wherein
$R^1$ is hydrogen, halogen, or alkyl or alkoxy containing from 1 to 4 carbon atoms,
$R^2$ is hydrogen, halogen, hydroxy or alkyl of alkoxy containing from 1 to 4 carbon atoms,
n and m are integers such that the sum (n+m) lies in the range from 3 to 10 inclusive and n differs from m, and
x is alkyl containing from 1 to 4 carbon atoms, hydrogen or a cation which is a metal cation of main Groups 1, 2 and 3 of the Periodic System of the Elements, an organic base cation or an ammonium ion. These compounds have pharmaceutical utility by virtue of their considerable ability to reduce the level of fatty substances in the blood.

5 Claims, No Drawings

PHENOXY ALKANOIC ACID DERIVATIVES HAVING THE ABILITY TO LOWER THE LEVEL OF FATTY SUBSTANCES IN THE BLOOD

This application is a continuation-in-part of our co-pending application Ser. No. 536,120 filed Dec. 24th, 1974, now abandoned.

This invention relates to novel benzylphenoxyalkanoic acids and esters and salts thereof, to methods for the preparation thereof, to pharmaceutical compositions comprising the same and to the use of the compounds in reducing cholesterol and triglyceride levels in blood.

Aryloxy carboxylic acid esters have been proposed for use in the therapy of excessive cholesterol and triglyceride levels in the blood in British patent specification No. 860,303. One of the substances described in British patent specification No. 860,303, namely the methyl ester of 2-(4'-chlorophenoxy)-isobutyric acid having the short name "Clofibrat" as recommended by World Health Organisation, has so far acquired considerable importance in the clinical treatment of human beings. It has since been found that many new compounds of related structure are superior to Clofibrat in their cholesterol-reducing effect to a surprisingly high extent. Phenoxy-alkanoic acids and esters thereof of such type are described, for example, in U.S. Pat. Nos. 3,546,273 filed 1st June, 1967 and 3,948,973 which is a continuation-in-part of Ser. No. 284,577 filed Aug. 29th, 1972.

More recently, attention has turned to the effect of benzyl phenoxy alkanoic acids and esters thereof in the therapy of excessive cholesterol and triglyceride levels in the blood. Compounds of this type were described as long ago as 1954 in British patent specification No. 705,251 which discloses such compounds as methyl 2-benzyl-4-chloro-phenoxy acetate in which the acetyloxy group is usually situated in a non-para position in the phenoxy ring. No activity in the therapy of excessive cholesterol and triglyceride levels in the blood has been attributed to any of the compounds disclosed in British patent specification No. 705,251. More recently, 4-substituted phenoxy isobutyric acid derivatives have been described by F. Miyoshi, H. Fukami and Y. Sako in J. Pharm. Soc. Japan 94 (9) 1061–1069 (1974) and also in German Offenlegungsschrift No. 2,356,655 as having hypocholesterolaemic and hypolipaemic activity. These compounds possess the general formula

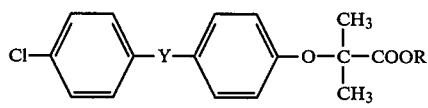

wherein Y is —CH$_2$—, —CH$_2$O—, —CH$_2$CH$_2$— or —CH=CH— and R is hydrogen or an alkyl group containing from 1 to 6 carbon atoms or an aminoalkyl group.

It has now been found that compounds having hypocholesterolaemic and hypolipaemic activity substantially greater than compounds mentioned in any of the aforesaid publications possess the general formula

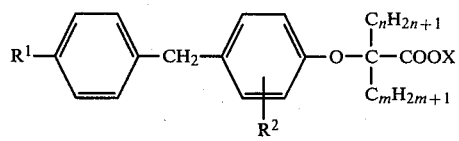

wherein
$R^1$ is hydrogen, halogen, or alkyl or alkoxy containing from 1 to 4 carbon atoms,
$R^2$ is hydrogen, halogen, hydroxy or alkyl or alkoxy containing from 1 to 4 carbon atoms,
n and m are integers such that the sum (n+m) lies in the range from 3 to 10 inclusive and n differs from m, and
X is alkyl containing from 1 to 4 carbon atoms, hydrogen or a cation which is a metal cation of main Groups 1, 2 and 3 of the Periodic system of the elements,
an organic base cation or an ammonium ion.

This invention also provides a process for the production of a compound according to the present invention wherein a phenol of the general formula

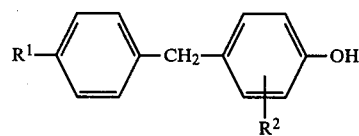

wherein $R^1$ and $R^2$ have the meanings set out hereinabove, or a corresponding alkali metal or alkaline earth metal phenolate is reacted with a compound of the general formula

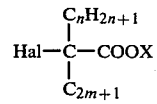

wherein "Hal" is a halogen atom and n, m and X have the meanings set out hereinabove, and recovering the said compound.

The compounds of this invention may also be produced by a method wherein a phenol of the general formula

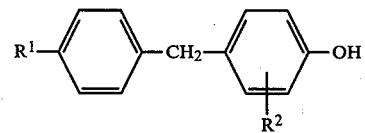

wherein $R^1$ and $R^2$ have the meaning set out hereinabove, or a corresponding alkali metal or alkaline earth metal phenolate is reacted in the presence of an at least trihalogenated methane derivative and in the presence of a strong base with a ketone of formula

wherein n and m have the aforesaid meanings and, depending on the nature of X in the aforesaid formula II,
(a) if necessary esterifying a carboxyl group in the reaction product so obtained or obtained by alkaline hydrolysis of a reaction product so obtained with a hydroxy terminated compound X′—OH, in which the group X′ is an alkyl group containing from 1 to 4 carbon atoms; or (b) when the reaction product of the compound of general formula III, the trihalogenated methane derivative and the ketone contains an alkoxy carbonyl group, subjecting the reaction product to ester exchange to yield a product containing a group X′—OCO— wherein X′ has the aforesaid meaning.

As previously indicated, with compounds according to the invention, $R^1$ and $R^2$ can be, inter alia, halogen atoms. They may be fluorine, chlorine, bromine or iodine, but are preferably chlorine. $R^1$ and $R^2$ may also be alkyl containing from 1 to 4 carbon atoms, more particularly methyl, ethyl, n-propyl or isopropyl, or n-butyl, isobutyl or t-butyl, or alkoxy of such carbon atom number, $R^2$ may be in the ortho or meta position with regard to the methylene group linking the two benzene rings.

A characteristic feature of the compounds of this invention is that the carbon atom lying between the ether oxygen atom and the carboxyl group is asymmetric. For this purpose, two alkyl groups which differ in their carbon atom content and which contain at least one carbon atom such that the total carbon atom content of the two alkyl groups is not more than 10 are linked to this carbon atom. Such alkyl groups can thus be methyl, ethyl, n-propyl or isopropyl, n-butyl, isobutyl or t-butyl or any of the pentyl, hexyl, heptyl, octyl or nonyl groups. The alkyl groups preferably contain from 1 to 4 carbon atoms. The nature of the optical isomerism based on the carbon atom linking the ether oxygen atom and the carboxyl group is not critical. Both D- and L-forms of the compound as well as racemates thereof possess hypocholesterolaemic and hypolipaemic activity.

The compounds of this invention may be either in free acid form or in the form of ester or salt. The effectiveness of the compounds is the same since it is believed that the active ingredient is the free acid and the salt forming cation or esterifying group simply determines the rate at which free acid is provided in the blood stream.

Alkyl groups X can be methyl, ethyl, n-propyl, isopropyl, n-butyl, isobutyl or t-butyl. When X is a metal cation, it can be an alkaline earth metal, for example sodium, potassium or lithium, an alkaline earth metal, for example magnesium, calcium, strontium or barium or a metal of the third main group of the Periodic system of the elements, in particular aluminium. Insofar as X may be designated by a polyvalent cation, it should be appreciated that what is in fact meant here is ½M++ or ⅓M+++ depending upon the valency of the metal M.

X may also be a cation of an organic base or ammonia. Examples of such cations are piperazinium, methyl thiazolinium, morpholinium, diethyl-hydroxyethyl ammonium, diethylammonium, diethanolammonium and ammonium.

As will be appreciated from the foregoing, two basic preparative methods have been found to be particularly satisfactory for use in the production of compounds according to the invention.

In the first such method, a phenol is reacted with a compound of general formula IV hereinabove. The halogen atom in the compound of general formula IV is preferably chlorine or bromine. Thus, for example, the compound 4-(4′-chlorobenzyl)-phenol can be condensed with the ethyl ester of 2-bromo-2-methylbutyric acid and the condensation products thereby obtained can be subjected to hydrolytic cleavage of the ethyl group to form 2-[4-(4′-chlorobenzyl)-phenoxy]-2-ethylbutyric acid. The reaction sequence may be terminated at this stage or if a reaction product in which X is an alkyl group other than ethyl or a cation is to be obtained, this compound can be subjected to further reaction. Thus for esterification purposes, this acid can be reacted with thionyl chloride to form its acid chloride which can be esterified by reaction with an alcohol containing from 1 to 4 carbon atoms.

In the second aforesaid process for the production of the compounds according to the present invention, a phenol of general formula III is reacted with a ketone of formula V in the presence of an at least trihalogenated methane derivative. When the trihalogenated methane derivative is a simple halomethane, for example chloroform or carbon tetrachloride, the reaction product will possess the general formula

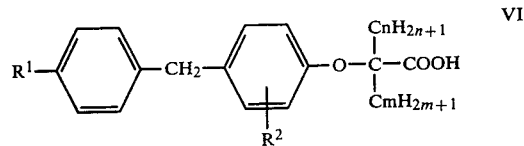

VI

When a substituted trihalogenated methane is used, the substituent will esterify the carboxyl group in the above formula. The product obtained in either case may be utilised as such as a compound according to the present invention. Alternatively, it may be converted to an alternative carboxyl derivative as aforesaid.

In an alternative reaction sequence applicable in the case when the trihalogenated methane derivative reacted with the phenol in the presence of the ketone and a strong base which can be sodium or potassium hydroxide contains a fourth substituent which is not a halogen atom and the product contains an alkoxy carbonyl group, the reaction product can be subjected then to ester exchange with a corresponding ester depending upon the nature of the group X in the final product.

Compounds of the general formula II have been found to be particularly effective agents for lowering the cholesterol level of blood. Although as mentioned above, aryloxy- and benzylaryloxy carboxylic acid esters have been proposed for use in the therapy of excessive cholesterol and triglyceride levels in the blood in for example British patent specification No. 860,303 and German Offenlegungsschrift No. 2,356,655, the compounds of the present invention are generally more effective.

Results of tests carried out on animals are set out in the following table, these results having been obtained with a representative selection of compounds according to this invention in comparison with Clofibrat (Comparative Product A) and the compound 2-[4-(4′-chlorobenzyl)-phenoxy]-2-methylpropionic acid ethyl ester, a compound according to German Offenlegungsschrift No. 2356655 (Comparative Product B). In the table which follows, the various columns are given reference numerals having the following meanings:

(1) Sets out the identification number of the test substance in question;
(2) Indicates the nature of the group etherifying a hydroxy alkanoic acid or ester or salt thereof;

(3) and (4) Denote the alkyl groups linked to the carbon atom which links the ether oxygen atom to the group —COOX;

(5) Denotes the nature of the symbol "X";

(6) Denotes the quantities of the test substance in mg/kg of body weight of the animal—rat (a) or mouse (b) which were orally administered to the test animals in tests to determine the acute toxicity LD50 therefor;

(7) Shows the quantities of the test substance in mg/kg of body weight of rats undergoing tests which were orally administered thereto to determine the daily dose which lowers the serum cholesterol level by 25% (ED25). Indicated in columns (8) and (9) are the therapeutic index values calculated from the numerical values of the preceding columns, that is to say the LD50$_{rat}$ED25$_{rat}$ and LD50$_{mouse}$/ED25$_{rat}$ ratios, respectively.

In column 2 the meanings of the symbols employed are as follows:

α = p-benzyl phenyl

β = p—(p'-chlorobenzyl)—phenyl

To determine the LD50 values, tests were carried out using male animals. After a single administration of the test substances, the animals were observed, their body weight being monitored, for at least seven days until toxic symptoms had faded. The volume of substances injected amounted to 10 ml/kg.

To determine the ED25 values set out in the Table, male rats weighing 100–200 g were given the test substance once daily orally, emulsified in 3% gum arabic in a volume of 1 ml/100 g body weight. Administration was usually commenced on Monday and continued up to and including Thursday of a second week. The final treatment on the Thursday was given at about 16.00 hours. Then the rats, which throughout the experient had been kept in dosage groups of 8–10 in size 3 Makrolon cages, were kept fasting. On the Friday morning, the animals were sacrificed by carotid section under ether narcosis. After centrifugation of the blood obtained in this way, the total cholesterol content of the serum was determined on a Beckman or DBG spectrophotometer by the method of Richterich, R. (Clinical Chemistry, S. Karger,/New York 1965, p.232). The average group values of Table were compared with those from a simultaneously investigated control group.

way of example, hypotriglyceridaemia produced in rats by adding fructose to their drinking water was lowered by Clofibrat administered in a dosage of 85 mg/kg by 25% per oral administration, whereas only 4.5 mg/kg of compound No.24774 were required to achieve the same effect.

It will be appreciated that for therapeutic use, the compounds of the invention can be made up, in accordance with well known pharmaceutical techniques, into compositions having as an essential active ingredient a compound of the invention in association with a pharmaceutical carrier therefor. If desired, the compositions can be made up in a dosage unit form suitable for the particular mode of administration, the quantity of active ingredient in each dosage unit being such that one or more units are required for each therapeutic administration. The dosage unit may exist, for example, in the form of a tablet, sugar coated pill, capsule or packaged powder for oral administration, or in the form of a sterile injectable solution or suspension, if desired contained in an ampoule, for parenteral administration. The dosage unit preferably contains from 5 to 300 milligrams of active substance. The compounds of the present invention may also be incorporated in emulsions or solutions for oral administration. For a person of average build, it is expected that a dosage of from 0.02 to 1.5 gram per day would be suitable for therapeutic purposes.

The following examples illustrate the invention. Although detailed examples only describe the preparation of a small number of compounds according to the present invention, further compounds have been prepared whose properties are summarised at the end of the examples.

EXAMPLE 1

2-Methyl-2-[4'-(4'-chlorobenzyl)-phenoxy]-butyric acid ethyl ester

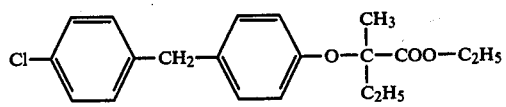

87.0 g (0.4 mol) of 4-chloro-4'-hydroxydiphenylmethane are heated together with 27.0 g (0.2 mol) of anhydrous potassium carbonate in 350 ml of anhydrous xylene for 30 minutes to reflux temperature, whereafter a solution of 83.5 g (0.4 mol) of 2-bromo-2-ethyl-2-methyl acetic acid ethyl ester in 50 ml of anhydrous xylene is

TABLE

| (1) | (2) | (3) | (4) | (5) | (6)(a) | (6)(b) | (7) | (8) | (9) |
|---|---|---|---|---|---|---|---|---|---|
| Comparative Product A | | | | | — | 2350 | 160 | — | 15 |
| Comparative Product B | | | | | — | 3000 | 54 | — | 120 |
| 24774 | β | CH$_3$ | C$_2$H$_5$ | C$_2$H$_5$ | 10000 | C. 10000 | 6 | 1667 | 1667 |
| 7275 | α | CH$_3$ | CH$_2$CH$_2$CH$_3$ | C$_2$H$_5$ | 10000 | 7600 | 0.7 | 14300 | 10800 |
| 8276 | β | CH$_3$ | CH$_2$CH$_2$CH$_2$CH$_3$ | C$_2$H$_5$ | 5000 | 3000 | 6.5 | 7769 | 462 |
| 9075 | β | CH$_3$ | C$_2$H$_5$ | CH$_2$CH$_2$CH$_3$ | — | 7900 | 10 | — | 790 |
| 9175 | β | CH$_3$ | C$_2$H$_5$ | CH$_3$ | — | 4750 | 9 | — | 528 |
| 8975 | β | CH$_3$ | C$_2$H$_5$ | CH$_2$CH$_2$CH$_3$ | — | 5300 | 34 | — | 156 |
| 33474 | β | CH$_3$ | CH$_2$CH$_2$CH$_3$ | C$_2$H$_5$ | 7350 | 5900 | 11.9 | 618 | 496 |
| 20776 | β | CH$_3$ | C$_2$H$_5$ | (CH(CH$_3$))$_2$ | — | 10000 | 31 | — | 323 |
| 32574 | α | CH$_3$ | C$_2$H$_5$ | C$_2$H$_5$ | 6100 | C. 9000 | 4.0 | 1525 | 2250 |

In addition to possessing the strong hypocholesterolaemic effect which can be seen from the table, the compounds of the present invention also lower considerably the triglyceride content of the blood and are in this respect again many times better than Clofibrat. By added. The mixture is kept for 24 hours and with vigorous stirring at reflux temperature. After filtering off the precipitated potassium bromide and evaporating the solvent in a Buchi rotary evaporator, the residue is taken up in ether and extracted with normal sodium hydroxide solution. The ether extracts are washed with water, dried over MgSO₄ and concentrated by evaporation. The brown oil (82.0 g) thereby obtained is dissolved in n-hexane and filtered through a column of 200 g of basic Al₂O₃. After evaporating the solvent and distillation at reduced pressure, 34.7 g of pure product are obtained with the boiling point 200°–204° C./0.01–0.1 mm Hg.

$C_{20}H_{23}ClO_3$: (346.8),

Calculated: C 69.25; H 6.68; O 13.84; Cl 10.22; Found: C 69.16; H 6.66; O 13.84; Cl 10.27.

The analogous product without chlorine substituent shows a boiling point of 154°–162° C./0.03 mm Hg ("Sgd 32574").

EXAMPLE 2

2-Methyl-2-[4-(4′-chlorobenzyl)-phenoxy]-valeric acid ethyl ester

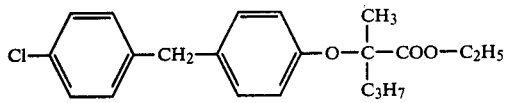

8.7 g (0.04 mol) of 4-chloro-4′-hydroxydiphenylmethane and 2.76 g (0.02 mol) of K₂CO₃ are brought over a period of 30 minutes to reflux temperature in 40 ml of anhydrous mesitylene-(1,3,5-trimethylbenzene), whereafter a solution of 8.9 g (0.04 mol) of 2-bromo-2-methyl-2-propyl acetic acid ethyl ester in 10 ml of anhydrous mesitylene is added and kept for another 24 hours and while stirring at reflux temperature. By working up in a manner similar to that indicated in the preceding Example 1 4.0 g of product are obtained as an oil with a boiling point of 177°–179° C./0.01 mm Hg.

$C_{21}H_{25}ClO_3$: (360.8),

Calculated: C 69.89; H 6.98; Cl 9.83; Found: C 70.00; H 7.23; Cl 9.37.

EXAMPLE 3

2-Methyl-2-[p-(p′-chlorobenzyl)phenoxy]butyric acid 20.80 g (0.095 mol) of 4′-chloro-4-hydroxydiphenylmethane are dissolved in 400 g (5.55 mol) of ethyl methyl ketone and stirred. 61.5 g (1.10 mol) of potassium hydroxide are added to the clear, colourless solution which is then stirred for 10 minutes. While the suspension obtained is undergoing stirring, 35.0 g (0.29 mol) of chloroform are added dropwise thereto. The temperature of the suspension increases from 24° to 26° C. After completion of addition of chloroform, stirring is continued for 5 minutes. The suspension becomes denser but more finely divided. The suspension is then heated to 50° C. and stirred for 4 hours at this temperature, the highest temperature recorded being 54° C. The suspension becomes dense and yellow.

The suspension is totally evaporated on a Büchi rotation evaporator at 50° C. using a water jet vacuum. The compact yellow residue is dissolved in 250 ml water. The dark solution obtained is mixed with 1 gram of active carbon and stirred for 10 minutes. The suspension obtained is filtered over Decalite. This brown, aqueous solution is acidified with 2N—HCl and extracted twice with 250 ml quantities of ether. The ethereal phase is then extracted twice with 200 ml samples of 10% sodium carbonate solution.

The two alkaline phases are purified, acidified with 2N HCl and extracted twice with 250 ml batches of ether. The ethereal extracts are dried over magnesium sulphate, filtered and completely evaporated on a Büchi rotation evaporator over a bath having a temperature of 40° C. 25 g of a dark brown very viscous oil are obtained. This crude product is dissolved in 10 ml of n-hexane and the solution is subjected to column chromatography using a column containing 75 g of silica gel (woelm: activity III/30 mm), the column having a diameter of 20 mm. Elution is effected using n-hexane in 250 ml quantities. Four fractions are obtained in this way, the first being colourless, the second yellow, and the third and fourth being colourless. Fractions 1, 2 and 4 are purified and completely evaporated on a Büchi rotation evaporator at a bath temperature of 50° C. 14 gram of a yellow oil are obtained representing a 46.6% yield. Analysis showed the product obtained to be 2-methyl-2-[p-(p′-chlorobenzyl)phenoxy]butyric acid.

Other compounds according to the present invention which have been produced by the procedures of Examples 1 and 2 have been the following:

I. Ethyl 2-methyl-2-(p-benzylphenoxy) valerate
II. Ethyl 2-methyl-2-[p-(p′-chlorobenzyl)phenoxy-o-methyl]butyrate (boiling point 184°–186° C./0.001 mm.Hg
III. Ethyl 2-methyl-2-[p-(p′-chlorobenzyl)phenoxy-m-methyl]butyrate (boiling point 154° C./0.01 mm Hg)
IV. Ethyl 2-methyl-2-[p-(p′-chlorobenzyl)phenoxy]hexanoate (boiling point: 180°–185° C.)
V. n-Propyl 2-methyl-2-[p-(p′-chlorobenzyl)phenoxy]butyrate (boiling point: 172°–190° C./0.001 mm.Hg)
VI. Methyl 2-methyl-2-[p-(p′-chlorobenzyl)phenoxy]butyrate (boiling point 173°–185° C./0.01 mm.Hg)
VII. n-Butyl 2-methyl-2-[p-(p′-chlorobenzyl)phenoxy]butyrate (boiling point: 175° C./0.001 mm.Hg)
VIII. t-Butyl 2-methyl-2-[p-(p′-chlorobenzyl)phenoxy]butyrate (melting point 52°–54° C.)
IX. Isopropyl 2-methyl-2-[p-(p′-chlorobenzyl)-phenoxy]butyrate (boiling point 196°–198° C./0.01 mm.Hg)
X. The sodium salt of 2-methyl-2-[p-(p′-chlorobenzyl)phenoxy]butyric acid In the cases of each of the aforesaid compounds, the structure of the product obtained was confirmed both by elemental analysis and by spectrographic analysis.

In the case of compound X the ethyl ester of 2-methyl-2-[p-(p′-chlorobenzyl)phenoxy]butyric acid prepared in Example 1 was hydrolysed in the presence of sodium hydroxide.

We claim:

1. Compounds of the general formula

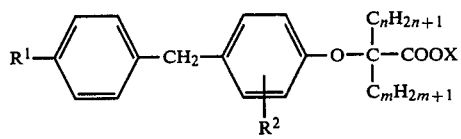

wherein
R¹ is hydrogen, halogen or alkyl or alkoxy containing from 1 to 4 carbon atoms;
R² is hydrogen, halogen, hydroxy or alkyl or alkoxy containing from 1 to 4 carbon atoms;

n and m are integers of from 1 to 4 such that the sum of n+m is from 3 to 7 inclusive with n differing from m; and X is alkyl containing from 1 to 4 carbon atoms.

2. Compounds of the general formula:

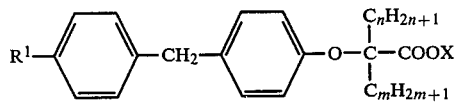

wherein
  $R^1$ is hydrogen or chlorine
  n and m are whole numbers of from 1 to 4, are different and such that the sum n+m is at least 3, and
  X is alkyl containing from 1 to 4 carbon atoms.

3. The compound of claim 1 which is 2-methyl-2-[p-(p'-chlorobenzyl)-phenoxy]-butyric acid ethyl ester.

4. The compound of claim 1 which is 2-methyl-2-(p-benzylphenoxy) butyric acid ethyl ester.

5. The compound of claim 1 which is 2-methyl-2-[4-(4'-chlorobenzyl)-phenoxy]-valeric acid ethyl ester.

* * * * *